United States Patent [19]

Rose

[11] Patent Number: 4,639,460

[45] Date of Patent: Jan. 27, 1987

[54] FUNGICIDAL SUBSTITUTED N-(1-IODOPROPARGYL)THIAZOLIDI-NONES

[75] Inventor: Bernard F. Rose, Walnut Creek, Calif.

[73] Assignee: Chevron Research Company, San Francisco, Calif.

[21] Appl. No.: 845,160

[22] Filed: Mar. 27, 1986

Related U.S. Application Data

[63] Continuation-in-part of Ser. No. 762,660, Aug. 5, 1985, which is a continuation of Ser. No. 629,657, Jul. 11, 1984, abandoned.

[51] Int. Cl.$^4$ .................... C07D 277/14; A01N 43/78
[52] U.S. Cl. ..................................... 514/369; 548/182
[58] Field of Search .......................... 548/182; 514/369

[56] References Cited

FOREIGN PATENT DOCUMENTS 1011845 12/1965 United Kingdom ................ 548/182

*Primary Examiner*—Robert Gerstl
*Attorney, Agent, or Firm*—S. R. LaPaglia; E. J. Keeling; S. L. Biggs

[57] ABSTRACT

Compounds of the formula:

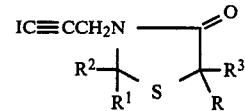

wherein R is hydrogen, lower alkyl; or aryl or aralkyl having from 6 to 12 carbon atoms, optionally substituted with one to three substituents, each independently selected from halogen, cyano, lower alkyl, lower alkoxy, nitro or trihalomethyl; $R^1$ is alkyl having from 1 to 12 carbon atoms, cycloalkyl having from 3 to 8 carbon atoms; aryl or aralkyl having from 6 to 12 carbon atoms optionally substituted with one to three substituents, each independently selected from halogen, cyano, lower alkyl, lower alkoxy, nitro, trihalo-substituted methyl, phenyl, phenoxy, substituted phenoxy substituted with 1 to 3 substituents independently selected from halogen, lower alkyl, lower alkoxy or trihalomethyl, benzyloxy, lower alkylthio, lower alkylsulfinyl, lower alkylsulfonyl, arylthio ($C_6$ to $C_{12}$), or two lower alkoxy groups joined to give an alkylene bridge; or thiophene or furanyl either optionally substituted with 1 to 3 substituents independently selected from halogen, trihalomethyl, lower alkyl, lower alkoxy; $R^2$ is hydrogen, lower alkyl, cycloalkyl having from 3 to 8 carbon atoms, or aryl or aralkyl having from 6 to 12 carbon atoms optionally substituted with one to three substituents, each independently selected from halogen, cyano, lower alkyl, lower alkoxy, nitro or trihalomethyl; and $R^3$ is hydrogen or lower alkyl are fungicidal.

25 Claims, No Drawings

FUNGICIDAL SUBSTITUTED N-(1-IODOPROPARGYL)THIAZOLIDINONES

REFERENCE TO RELATED APPLICATIONS

This application is a continuation-in-part of application Ser. No. 762,660 filed Aug. 5, 1985 which is a continuation of U.S. Ser. No. 629,657 filed July 11, 1984, now abandoned.

BACKGROUND OF THE INVENTION

The present invention relates to substituted N-(1-iodopropargyl)thiazolidinones which have fungicidal activity.

In a world which has an ever-increasing population which is dependent for food on a ever-decreasing amount of arable land, it is important to develop agents which may help to increase crop yields. For example, fungicides may increase crop production by protecting crops from destruction by fungi, including plant fungal diseases.

SUMMARY OF THE INVENTION

The fungicidal substituted N-(1-iodopropargyl)-thiazolidinones of my invention have the general formula:

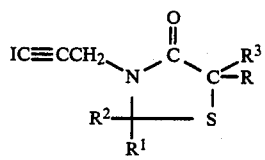

wherein R is hydrogen, lower alkyl; or aryl or aralkyl having from 6 to 12 carbon atoms, optionally substituted with one to three substituents, each independently selected from halogen, cyano, lower alkyl, lower alkoxy, nitro or trihalomethyl; $R^1$ is alkyl having from 1 to 12 carbon atoms, cycloalkyl having from 3 to 8 carbon atoms; aryl or aralkyl having from 6 to 12 carbon atoms optionally substituted with one to three substituents, each independently selected from halogen, cyano, lower alkyl, lower alkoxy, nitro, trihalo-substituted methyl, phenyl, phenoxy, substituted phenoxy substituted with 1 to 3 substituents independently selected from halogen, lower alkyl, lower alkoxy or trihalomethyl, benzyloxy, lower alkylthio, lower alkylsulfinyl, lower alkylsulfonyl, arylthio ($C_6$ to $C_{12}$), or two lower alkoxy groups joined to give an alkylene bridge; or thiophene or furanyl either optionally substituted with 1 to 3 substituents independently selected from halogen, trihalomethyl, lower alkyl, lower alkoxy; $R^2$ is hydrogen, lower alkyl, cycloalkyl having from 3 to 8 carbon atoms, or aryl or aralkyl having from 6 to 12 carbon atoms optionally substituted with 1 to 3 substituents, each independently selected from halogen, cyano, lower alkyl, lower alkoxy, nitro or trihalomethyl; and $R^3$ is hydrogen or lower alkyl.

Among other factors, the present invention is based on my finding that the compounds of this invention are surprisingly effective in controlling fungi, especially fungi which may cause plant fungal diseases.

Representative R groups include hydrogen, methyl, isopropyl and p-chlorophenyl.

Representative $R^1$ groups include n-hexyl, 2-ethoxyphenyl, 2,4-dimethoxyphenyl, 3-chlorophenyl, 4-chlorophenyl, naphthyl, 4-cyanophenyl, and 3-nitrophenyl.

Representative $R^2$ groups include hydrogen, methyl, and p-chlorophenyl. Representative $R^3$ groups include hydrogen, methyl and isopropyl.

Preferred R groups include hydrogen, and methyl.
Preferred $R^1$ groups include 4-chlorophenyl, 2-ethoxyphenyl, and 1-naphthyl.
Preferred $R^2$ groups include hydrogen, and methyl.
Preferred $R^3$ groups include hydrogen.
Representative compounds of this invention are included in Table I.

DEFINITIONS

As used herein, the following terms have the following meanings, unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "alkylene" refers to the group -$(CH_2)_m$- wherein m is an integer greater than zero. Typical alkylene groups include methylene, ethylene, propylene and the like.

The term "alkenyl" refers to unsaturated alkyl groups having a double bond [e.g., $CH_3CH=CH(CH_2)_2-$] and includes both straight- and branched-chain alkenyl groups. "Lower alkenyl" refers to groups having a total of from 3 to 6 carbon atoms. Typical lower alkenyl groups include, for example, propenyl, but-3-enyl, hex-4-enyl, 2-methylpent-4-enyl, and the like.

The term "halo" or "halogen" refers to the groups fluoro, chloro, bromo and iodo.

The term "alkoxy" refers to the group R'O— wherein R' is alkyl. The term "lower alkoxy" refers to alkoxy groups having from 1 to 6 carbon atoms; examples include methoxy, ethoxy, hexoxy, and the like.

The term "hydroxy alkyl" refers to the group —R''-'OH wherein R'' is branched or unbranched alkylene and the hydroxy can be on a primary, secondary or a tertiary carbon. Examples include hydroxy ethyl and 2-hydroxypropyl and 2-hydroxy-2-methyl butyl.

The term "aryl" refers to aryl groups having from 6 to 12 carbon atoms and includes, for example, phenyl, naphthyl, indenyl, and the like. Typically, the aryl group will be phenyl or naphthyl, as compounds having such groups are more readily available commercially than other aryl compounds.

The term "substituted aryl" refers to aryl groups having 1 to 3 substituents independently selected from the group of lower alkyl, lower alkoxy, halogen, cyano, nitro, trihalo-substituted methyl, phenyl, phenoxy, substituted phenoxy, benzyloxy, lower alkylthio, lower alkylsulfinyl, lower alkylsulfonyl, arylthio ($C_6$ to $C_{12}$) or two lower alkoxy groups joined to give an alkylene bridge. Typical substituted aryl groups include, for example, 2-fluorophenyl, 2-chlorophenyl, 2,6-dimethylphenyl, 4-fluorophenyl, 2-methylphenyl, 2-chloro,3-chloromethylphenyl, 2-nitro,5-methylphenyl, 2,6-dichlorophenyl, 3-trifluoromethylphenyl, 2-methoxyphenyl, 2-bromonaphth-1-yl, 3-methoxyinden-1-yl, and the like.

The term "aralkyl" refers to an alkyl group of 1 to 4 carbons substituted with an aryl group of from 6 to 12 carbons and includes, for example, benzyl, p-methylbenzyl and 2-phenylethyl.

The term "alkylthio" refers to the group R'S— wherein R' is alkyl. The term "lower alkylthio" refers to alkylthio groups having from 1 to 6 carbon atoms; examples include methylthio, ethylthio, n-hexylthio, and the like.

The term "arylthio" refers to the group R"S— wherein R" is an aryl group; examples include phenylthio, naphthylthio and the like.

DETAILED DESCRIPTION OF THE INVENTION

The compounds of the present invention may be conveniently prepared according to the following reaction scheme:

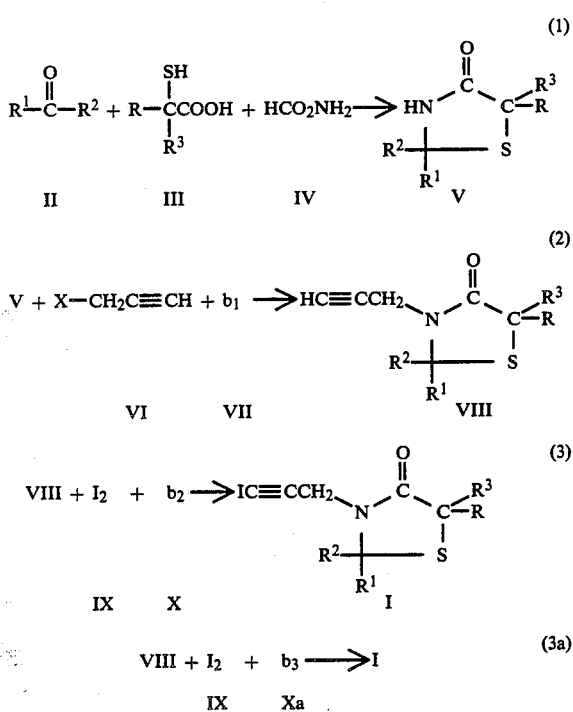

wherein R, $R^1$, $R^2$ and $R^3$ are as previously defined in conjunction with formula I, X is halogen, and $b_1$, $b_2$, and $b_3$ are bases.

Reaction (1) is conducted by combining approximately equimolar amounts of II, III and IV in solvent. The reaction is conducted at a temperature of from about 80° C. to about 150° C., preferably from about 100° C. to about 130° C. or at reflux; and is generally complete within about ½ to about 6 hours. Suitable solvents include inert organic solvents such as toluene, xylene, benzene, and the like. The product V is isolated by conventional procedures such as extraction, washing, filtration, stripping, hard-topping, and the like.

Reaction (2) is conducted by adding VI to a mixture of V and VII in solvent. It is preferred to first add V to a mixture of VII in solvent. The reaction is conducted at a temperature of about 0° C. to about 100° C., preferably from about 0° C. to about 50° C., and is generally complete within about 1 to about 24 hours. Preferably, approximately equimolar amounts of V, VI and VII may be used. Suitable bases $b_1$ include strong bases such as sodium hydride, alkyl lithium salts, potassium t-butoxide, and the like. Suitable solvents include inert organic solvents such as dimethoxyethane, ether, furan, dimethylformamide, and the like. Propargyl bromide is the preferred propargyl halide VI. The product VIII is isolated by conventional procedures such as extraction, stripping, chromatography, crystallization, and the like.

Reaction (3) is conducted by adding IX to a mixture of VIII and X in solvent. It is preferred to first add VIII to a mixture of X in solvent. The reaction is conducted at a temperature of about 0° C. to about 100° C., preferably from about 0° C. to about 80° C. or for convenience at ambient temperature, and is generally complete within about ½ to about 24 hours. Suitable bases $b_2$ include alkali metal alkoxides, such as sodium methoxide. Such alkoxides may be conveniently prepared in situ by adding alkali metal to alcohol which may then also act as solvent. Suitable alcohols include those having up to 4 carbon atoms such as methanol, ethanol, tert-butanol, and the like. The product I is isolated by conventional procedures such as extraction, washing, stripping, chromatography, hard-topping, crystallization, and the like.

Reaction (3a) is an alternate reaction scheme for adding the iodo group. Reaction (3a) is conducted by combining XV, IX and Xa in solvent. It is preferred to add IX to a stirring mixture of XV and Xa. It is preferred to add a slight excess of IX relative to XV on the order of about 1.05 to about 1.2 equivalents IX for equivalent XV. It is also preferred to add an excess of Xa relative to XV, on the order of about 2 to about 5 equivalents Xa per equivalent XV. Suitable bases $b_3$ include inorganic bases such as potassium carbonate, sodium hydroxide, and the like. Suitable solvents include benzene, toluene, dimethoxyethane, and the like. The reaction is conducted at a temperature of from about 20° C. to about 100° C., preferably from about 20° C. to about 40° C., and is generally complete within about 8 to about 24 hours. The product I is isolated by conventional procedures such as filtration, absorbing, stripping, recrystallization, and the like.

Alternatively, intermediate VIII may be prepared according to the following reaction scheme:

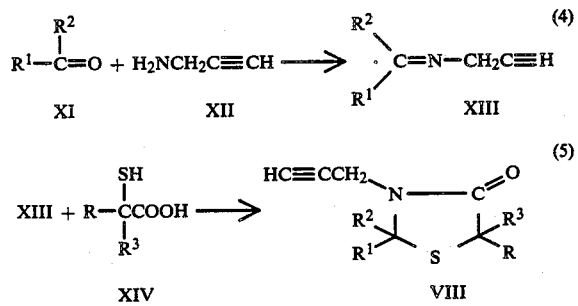

where R, $R^1$, $R^2$ and $R^3$ are as previously defined in conjunction with Formula I.

Reaction (4) is conducted by combining XI and XII. Although approximately equimolar amounts of XI and XII may be used, it is preferred to use a slight excess of XII relative to XI, on the order of about 1.05 to about 1.1 equivalents XII per equivalent XI. The reaction is conducted at a temperature of from about 80° C. to about 120° C., preferably from about 80° C. to about 90° C., or for convenience at reflux. The reaction is generally complete within about 1 to about 3 hours. It is preferred to use a trap, such as a Dean and Stark trap to collect water generated during the reaction. The product XIII is isolated by conventional procedures, such as stripping, trituration, filtration, precipitation, and the like.

Reaction (5) is conducted by combining approximately equimolar amounts of XIII and XIV in solvent. Preferably, the reaction is conducted in a nitrogen atmosphere. It is preferred to have the reaction vessel vented through a calcium hypochlorite solution to prevent escape of any of the highly odiferous mercaptan into the atmosphere. The reaction is conducted at a temperature of from about 70° C. to about 120° C., preferably from about 80° C. to about 90° C., or at reflux. The reaction is generally complete within about 1 to about 3 hours. The product VIII is isolated by conventional procedures, such as washing, extraction, stripping, filtration, distillation, and the like.

The intermediate VIII is then converted to the compounds of this invention as outlined in Reactions (3) and (3a).

UTILITY

The compounds of this invention are particularly effective in controlling plant fungal infections, especially late blights caused by organisms such as *Phytophthora infestans*. Some for controlling leaf blights caused by organisms such as *Alternaria solani conidia* and *Septoria apii* and downy mildews such as that caused by *Plasmopara viticola*. However, some compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other typs of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLE 1

Preparation of

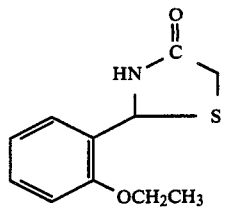

2-(2-ethoxyphenyl)thiazolidin-4-one

In a 3-neck flask equipped with a Dean & Stark trap for continuous collection and removal of water, heating mantle and condenser, 50 g (0.33 mole) O-ethoxybenzaldehyde, 31.3 g (0.33 mole) 98% mercaptoacetic acid and 21.6 g (0.33 mole) 97% ammonium formate in 200 ml toluene were placed. The reaction mixture was heated to reflux and then stirred at reflux about 3 hours until no more water was collecting in the trap. After the reaction mixture had been allowed to cool, it was poured into about 1000 ml water. Ethyl acetate (about 600 ml) was added and the resulting mixture was extracted. The organic phase was washed with an aqueous solution of potassium carbonate until neutralized. The mixture was washed with water, dried, filtered and stripped to give an amorphous yellow-orange semi-solid which was then washed with petroleum ether/ether to give the above-identified product as a yellow solid.

EXAMPLE 2

Preparation of

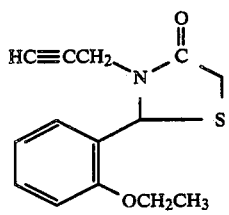

2-[2-ethoxyphenyl]-3-[3-propynyl]thiazolidin-4-one

To a mixture of 1.2 g (0.025 mole) sodium hydride in 75 ml dimethoxyethane, 5.5 g (0.025 mole) 2-[2-ethoxyphenyl]thiazolidin-4-one (the product of Example 1) were added. The resulting mixture was stirred 20 minutes at ambient temperature and then cooled to about 0° C. To the cooled mixture 3.8 g (0.025 mole) 78% propargyl bromide were added. The reaction mixture was stirred overnight at ambient temperature. The mixture was poured into water (about 1000 ml) and then extracted twice with ethyl acetate. The combined organic extracts were washed with water (about 500 ml), dried, filtered and stripped to give a brown oil. The brown oil was chromatographed on silica gel eluting with 30% ethyl acetate/hexane to give 4 g of the above-identified product as a light yellow oil.

EXAMPLE 3

Preparation of

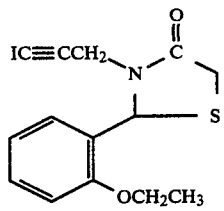

2-[2-ethoxyphenyl]-3-[1-iodo-3-propynyl]thiazolidin-4-one

To a mixture of 0.23 g (0.00957 mole) sodium metal in 100 ml methanol which had been cooled to about 0° C., 2.5 g (0.00957 mole) 2-[2-ethoxyphenyl]-3-[3-propynyl]-thiazolidin-4-one (the product of Example 2) in 20 ml methanol was added. The mixture was stirred about 5 minutes, then 24 g (0.00957 mole) iodine was added. Cooling was removed; the reaction mixture was allowed to warm to room temperature and then stirred overnight at ambient temperature. The reaction mixture was poured into water (about 500 ml) and then extracted with ethyl acetate. The ethyl acetate extract was washed with an aqueous bisulphite solution and with water, then dried, filtered and stripped to give a red oil. The oil was chromatographed on silica gel, eluting with 30% ethyl acetate/hexane to give 3.4 g of the above-identified product, as a red oil.

EXAMPLE 4

Preparation of

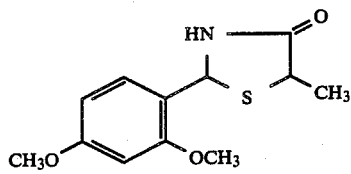

2-[2,4-Dimethoxyphenyl]-5-methylthiazolidin-4-one

In a flask equipped with a trap for the continuous collection and removal of water and condenser, 40 g (0.24 mole) 2,4-dimethoxybenzaldehyde, 26.8 g (0.24 mole) 95% thiolactic acid, 15.2 g (0.24 mole) ammonium formate and 200 ml toluene were placed. The resulting mixture was heated to reflux and refluxed for 4 hours, during which about 10 ml water were collected. The reaction mixture was then allowed to stir overnight without heat at ambient temperature. An orange precipitate formed overnight. The reaction mixture was poured into water and then extracted three times with ethyl acetate. The combined organic fractions were washed twice with an aqueous potassium carbonate solution, once with water, dried, and filtered. Stripping gave a yellow semi-solid which washed with ether to give 20 g of the above-identified product as a fluffy yellow solid.

EXAMPLE 5

Preparation of

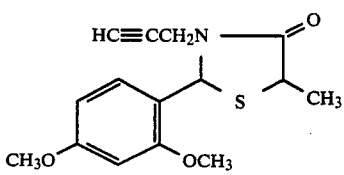

2-[2,4-dimethoxyphenyl]-3-[3-propynyl]-5-methylthiazolidin-4-one

To a mixture of 1.9 g (0.04 mole) 50% sodium hydride in 100 ml dimethoxyethane, 10 g (0.04 mole) 2-[2,4-dimethoxyphenyl]-5-methylthiazolidin-4-one (the product of Example 4) was added in portions. The resulting mixture was stirred at ambient temperature for 20 minutes. The mixture was cooled to about 0° C., then 5.9 g (0.04 mole) 80% propargyl bromide were added. The reaction mixture was kept cold, stirred at about 0° C. for 4 hours, allowed to warm to room temperature, and then stirred overnight at ambient temperature. The reaction mixture was poured into water and extracted twice with ethyl acetate. The combined organic fractions were washed with water, filtered, dried and stripped to give the above-identified products as a viscous yellow oil.

EXAMPLE 6

Preparation of

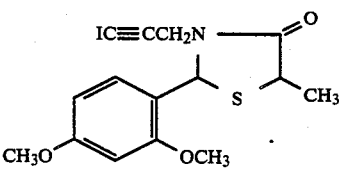

2-[2,4-dimethoxyphenyl]-3-[1-iodo-3-propynyl]-5-methylthiazolidin-4-one

To a mixture of 0.28 g (0.012 mole) sodium metal in 50 ml methanol which had been cooled to about 0° C., 3.5 g (0.012 mole) 2-[2,4-dimethoxyphenyl]-3-[3-propynyl]-5-methylthiazolidin-4-one (the product of Example 5) was added, followed by 3.1 g (0.012 mole) iodine. The reaction mixture was kept cold, stirred at about 0° C. for several hours and then stirred overnight at ambient temperature. The reaction mixture was poured into water and extracted twice with ethyl acetate. The organic phase (combined ethyl acetate extracts) was washed twice with an aqueous sodium bisulphite solution and once with water, dried, filtered and stripped to give a yellow oil. The oil was chromatographed on silica gel, eluting with 30% ethyl acetate/hexane to give 3 g of the above-identified product as a pale yellow viscous oil.

EXAMPLE 7

Preparation of

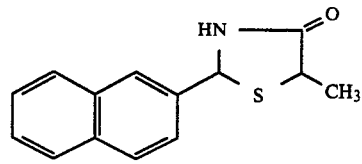

2-[1-Naphthyl]-5-methylthiazolidin-4-one

In a flask with a trap for continuous collection and removal of water, 31 g (0.19 mole) 1-naphthaldehyde, 21.5 g (0.19 mole) 95% thiolactic acid, 12 g (0.19 mole) ammonium formate and 200 ml toluene were combined. The mixture was heated to reflux and refluxed three hours. The reaction mixture was allowed to cool and then filtered. The solids were washed with petroleum ether and then ethyl ether and then air-dried to give 29 g of the above-identified product as a white solid.

EXAMPLE 8

Preparation of

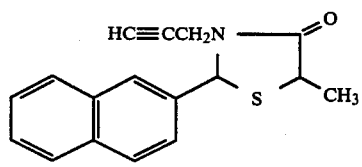

2-[1-Naphthyl]-3-[3-propynyl]-5-methylthiazolidin-4-one

To a mixture of 1.6 g (0.033 mole) 50% sodium hydride in 100 ml dimethoxyethane, 8 g (0.033 mole) 2-[1-naphthyl]-5-methylthiazolidin-4-one (the product of Example 7) was added in portions. The resulting mixture was stirred for 20 minutes and then cooled (to about 0°–5° C.), then 5.1 g (0.033 mole) 78% propargyl bromide was added. The reaction mixture was stirred overnight. The mixture was poured into water and then extracted twice with ethyl acetate. The combined organic fractions were washed with water, dried, filtered and stripped to give an orange oil. Chromatography of the oil on silica gel, eluting with 30% ethyl acetate/hexane gave 8 g of the above-identified product.

EXAMPLE 9

Preparation of

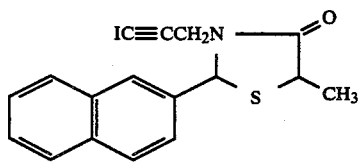

2-[1-Naphthyl]-3-[1-iodo-3-propynyl]-5-methylthiazolidin-4-one

To a mixture of 0.56 g (0.024 mole) sodium metal in 75 ml methanol, which had been cooled to about 0° C., 3.8 g (0.0135 mole) 2-[1-naphthyl]-3-[3-propynyl]-5- methylthiazolidin-4-one (the product of Example 8) were added, followed by 3.1 g (0.012 mole) iodine. The reaction mixture was stirred for about one-half hour at 0° C. The ice bath was removed and the reaction mixture was stirred at ambient temperature for one hour. The mixture was poured into water, giving a white precipitate, and extracted twice with ethyl acetate. The combined organic layers were washed with water, dried, filtered, stripped and hard-topped to give 5.5 g of the above-identified product as a viscous yellow oil which hardened and became brittle upon standing.

EXAMPLE 10

Preparation of

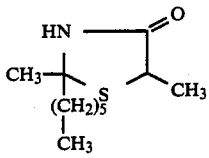

2-[1-(n-hexyl)]-2,5-dimethylthiazolidin-4-one

In a flask equipped with a trap for continuous collection and removal of water and a condenser, 50 g (0.389 mole) 2-octanone, 43.6 g (0.3899 mole) 95% thiolactic acid, 25 g (0.3899 mole) ammonium formate and 150 ml toluene were combined. The reaction was heated at reflux for three hours and then allowed to sit overnight; additional thiolactic acid (about 8.6 g) and ammonium formate (about 5 g) were added. The reaction mixture was heated at reflux an additional 3 hours and then allowed to cool. The reaction mixture was poured into water (about 1000 ml), ethyl acetate (about 200 ml) was added and then aqueous potassium carbonate until the pH was basic. The mixture was extracted three times with ethyl acetate. The combined ethyl acetate extracts were washed with water, dried, filtered, stripped and hard-topped to give 75.5 g of the above-identified product as an orange oil.

EXAMPLE 11

Preparation of

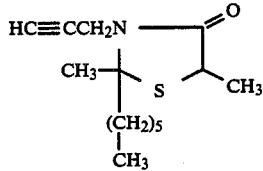

2-[1-(n-hexyl)]-2,5-dimethyl-3-[3-propynyl]thiazolidin-4-one

To a mixture of 3.3 g (0.0697 mole) 50% sodium hydride in about 75 ml dimethoxyethane, 15 g (0.0697 mole) 2-[1-(n-hexyl)]-2,5-dimethylthiazolidin-4-one (the product of Example 10) was added in portions. The resulting mixture was stirred for about 20 minutes, and then cooled to about 0° C. Then 10.4 g (0.0697 mole) 85% propargyl bromide was added. The reaction mixture was stirred at about 0° C. for several hours and then at ambient temperature overnight. The mixture was poured into water and then extracted twice with ethyl acetate. The combined organic fractions were washed with water, dried, filtered, stripped, and chromatographed on silica gel, eluting with 10% ethyl acetate/hexane to give 8 g of the above-identified product as a light yellow oil.

EXAMPLE 12

Preparation of

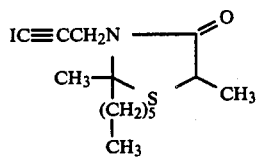

2-[1-(n-hexyl)]-2,5-dimethyl-3-[1-iodo-3-propynyl]-thiazolidin-4-one

To a mixture of 0.5 g (0.022 mole) sodium metal in 50 ml methanol which has been cooled to about 0° C., 5.5 g (0.022 mole) 2-[1-(n-hexyl)]-2,5-dimethyl-3-[3-propynyl]thiazolidin-4-one (the product of Example 11) was added, followed by 5.5 g (0.022 mole) iodine. The reaction mixture was stirred at about 0° C. for three hours and then allowed to stir overnight at ambient temperature. The mixture was poured into water at which point a white precipitate formed and then extracted three times with ethyl acetate. The organic extracts were washed twice with sodium bisulphite, once with water, dried, filtered and stripped to give 6 g of the above-identified product as a light brown oil.

EXAMPLE 13

Preparation of
2-[2,4-dichlorophenyl]-5-methylthiazolidin-4-one

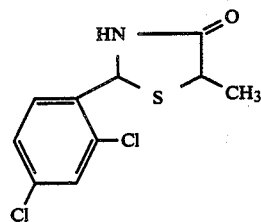

In a 500 ml 3-necked flask equipped with a Dean & Stark trap and reflux condenser, 30 g (0.17 mole) 2,4-dichlorobenzaldehyde, 18.2 g (0.17 mole) 95% thiolactic acid and 10.8 g (0.17 mole) ammonium formate in 150 ml toluene were placed. The reaction mixture was heated to reflux for several hours; 17 ml water collected. The mixture was at first clear in color and then turned yellow. The reaction mixture was allowed to sit overnight during which yellow solids precipitated. The mixture was filtered. The solids were washed with ether and then air dried to give 38 g of the above-identified product as a white solid.

Elemental analysis for $C_{10}H_7NOSCl_2$ showed: calculated %C 45.80, %H 3.44, and %N 5.34; found %C 44.97, %H 3.4, and %N 5.34.

EXAMPLE 14

Preparation of 2-[2,4-dichlorophenyl]-3-[3-propynyl]-5-methylthiazolidin-4-one

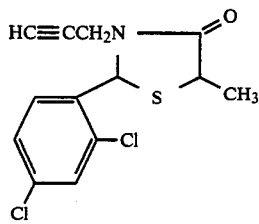

To a mixture of 1.3 g (0.027 mole) 50% sodium hydride in 65 ml dimethoxy ethane, 7 g (0.027 mole) 2-[2,4-dichlorophenyl]-5-methylthiazolidin-4-one (the product of Example 13) was added in portions. The mixture was allowed to stir for fifteen minutes, and then was cooled to 0° C. with an ice water bath. Then, 3.2 g (0.027 mole) propargyl bromide was added. After forty-five minutes a precipitate formed and the mixture had turned yellow. The mixture was kept cold for several hours and then stirred overnight at ambient temperature. The mixture was poured into water. The layers were phase separated. The aqueous phase was extracted with ethyl acetate. The ethyl acetate extract was washed once with water, dried, filtered and stripped. The residue was chromatographed, eluting first with 10% ethyl acetate hexane and then 30% ethyl acetate/hexane to give 4 g of the above-identified product as a viscous yellow oil.

Elemental analysis for $C_{13}H_9NOSCl_2$ showed: calculated %C 52.00, %H 3.67, and %N 4.67; found %C 51.05, %H 3.58, and %N 4.28.

EXAMPLE 15

Preparation of 2-[2,4-dichlorophenyl]-3-[1-iodo-3-propynyl]-5-methylthiazolidin-4-one

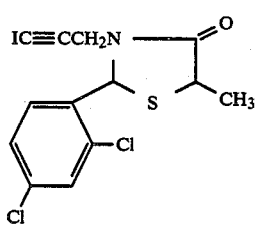

Sodium metal, 0.18 g (0.008 mole) was added to methanol (50 ml) in portions. When the sodium had dissolved, the mixture was cooled to 0° C. in an ice-water bath. Then 2.3 g (0.008 mole) 2-[2,4-dichlorophenyl]-3-[3-propynyl]-5-methylthiazolidin-4-one (the product of Example 14) and 1.9 g (0.008 mole) iodine were added. The mixture was kept cold for several hours and then stirred overnight at ambient temperature. The mixture was poured into water; a white precipitate formed. The mixture was extracted with ethyl acetate. The ethyl acetate extract was washed twice with aqueous sodium bisulfite, washed once with water, dried, filtered, stripped to give a yellow-brown oil. The oil was hard topped to give 3 g of the above-identified product as a brown oil.

Elemental analysis for $C_{13}H_8NOSCl_2I$ showed: calculated %C 36.62, %H 2.35, and %N 3.29; found %C 33.36, %H 2.53, and %N 2.64.

The compounds of this invention, may in the alternative, be prepared by the sequence demonstrated in Examples 16–18. This procedure is equally applicable to any of the materials of this invention and is not limited to the examples shown.

EXAMPLE 16

Preparation of N-propargyl-2,4-dichlorobenzylideneimine

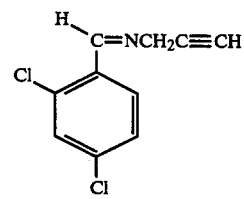

In a one-liter, 3-necked flask, equipped with a Dean and Stark trap, a reflux condenser, and a heating mantel, 100 g (0.57 mole) 2,4-dichlorobenzaldehyde, 34.6 g (0.629 mole) of propargylamine and 570 ml benzene were placed. The mixture was stirred and refluxed for 2.5 hrs. over which time 79.8 ml of water were collected. The mixture was stripped to afford a brown semisolid which was triturated with hexane/10% ethyl ether which had been cooled to 0° C. The resulting needle-like brown crystals were collected by filtration and used without further purification in the next step.

EXAMPLE 17

Preparation of 2-[2,4-dichlorophenyl]-3-[3-propynyl]-5-methylthiazolidin-4-one

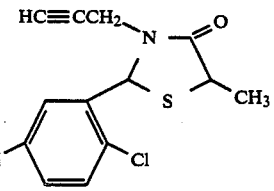

A 3-liter, 3-necked flask, equipped with a Dean and Stark trap, reflux condenser, heating mantel, and mechanical stirrer was placed under a nitrogen atmosphere which was vented through a calcium hypochloride (bleach) solution. A mixture of 180 g (0.839 mole) of the product of Example 16, 89 g thiolactic acid (0.839 mole), and 1500 ml benzene was placed in the flask and then refluxed for 3 hours over which time 13.9 ml of water were collected. The mixture was cooled to 0° C. and 1500 ml hexane was added. The mixture, which contained a small amount of flocculent material, was washed with saturated sodium bicarbonate, dried over magnesium sulfate, filtered through a Celite pad and stripped to afford an amber oil which compared favorably with the product of Example 14 by GC, nmr, and ir. The yield was 94.4%.

EXAMPLE 18

Preparation of
2-[2,4-dichlorophenyl]-3-[1-iodo-3-propynyl]-5-methylthiazolidin-4-one

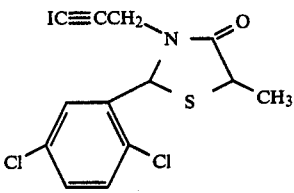

In a one-liter, 3-necked flask equipped with a mechanical stirrer 80.37 g (0.27 mole) of the product of Example 17 and 74 g (0.538 mole) potassium carbonate were placed. Vigorous stirring was begun and iodine 74.8 g (0.295 mol) was added rapidly in portions. A slight exotherm occurred (approximately 5° C.). The mixture was stirred for 18 hours during which time disappearance of the acetylenic proton at 2.58δ was followed by nmr. The mixture was filtered and the solids washed with ethyl acetate. The combined organic portions were washed twice with water, twice with saturated sodium bisulfite, then dried over magnesium sulfate, filtered, and stripped to afford a dark red oil containing some solids. The mixture was dissolved in a minimum amount of methylene chloride and then cooled to −78° C. Hexane was added slowly until a precipitate formed. The product was collected by filtration as a pale yellow-brown solid which was then recrystallized from ethanol to afford light beige crystals. The nmr and ir compared favorably with those of Example 15. The yield was 53%.

Elemental analysis for $C_{13}H_8NOSCl_2I$ showed: calculated %C 36.63; %H 2.35; %N 3.29; found %C 27.97, %H 2.49, %N 2.49.

Compounds made in accordance with the methods described in the Detailed Description of the Invention, Examples 1 to 18 are found in Table I.

By following the methods disclosed in the Detailed Description of the Invention and in Examples 1 to 15, the following compounds are made:

2-[4-chlorophenyl]-3-[1-iodo-3-propynyl]-5-isopropyl-thiazolidin-4-one;
2-[3,4-dichlorophenyl]-3-[1-iodo-3-propynyl]-5-isopropylthiazolidin-4-one;
2-[2-ethoxyphenyl]-3-[1-iodo-3-propynyl]-5-isopropyl-thiazolidin-4-one;
2-[1-naphthyl]-3-[1-iodo-3-propynyl]-5-isopropyl-thiazolidin-4-one;
2-[2-naphthyl]-3-[1-iodo-3-propynyl]-5-isopropyl-thiazolidin-4-one;
2-[2-naphthyl]-3-[1-iodo-3-propynyl]-5-methylthiazolidin-4-one;
2-[4-chlorophenyl]-3-[1-iodo-3-propynyl]-5-phenyl-thiazolidin-4-one;
2-[3,4-dichlorophenyl]-3-[1-iodo-3-propynyl]-5-phenyl-thiazolidin-4-one;
2-[2-ethoxyphenyl]-3-[1-iodo-3-propynyl]-5-phenyl-thiazolidin-4-one;
2-[1-naphthyl]-3-[1-iodo-3-propynyl]-5-phenylthiazolidin-4-one;
2-[2-naphthyl]-3-[1-iodo-3-propynyl]-5-phenylthiazolidin-4-one;
2-[4-chlorophenyl]-2,5-diphenyl-3-[1-iodo-3-propynyl]-thiazolidin-4-one;
2-[3,4-dichlorophenyl]-2,5-diphenyl-3-[1-iodo-3-propynyl]thiazolidin-4-one;
2,2-[di-2-ethoxyphenyl]-3-[1-iodo-3-propynyl]-5-phenylthiazolidin-4-one;
2,2,5-triphenyl-3-[1-iodo-3-propynyl]thiazolidin-4-one;
2,2-diphenyl-3-[1-iodo-3-propynyl]thiazolidin-4-one;
2-[2-ethoxyphenyl]-2-phenyl-3-[1-iodo-3-propynyl]-thiazolidin-4-one;
2,2-[di-2-ethoxyphenyl]-3-[1-iodo-3-propynyl]thiazolidin-4-one;
2,2-diphenyl-3-[1-iodo-3-propynyl]-5-methylthiazolidin-4-one;
2,2-[di-4-chlorophenyl]-3-[1-iodo-3-propynyl]-5-methylthiazolidin-4-one;
2-[3,4-dichloro]-2-phenyl-3-[1-iodo-3-propynyl]-5-methylthiazolidin-4-one;
2,2-diphenyl-3-[1-iodo-3-propynyl]-5-isopropylthiazolidin-4-one;
2,2-[di-4-chlorophenyl]-3-[1-iodo-3-propynyl]-5-isopropylthiazolidin-4-one;
2-[3,4-dichloro]-2-phenyl-3-[1-iodo-3-propynyl]-5-isopropylthiazolidin-4-one; and
2,2-[di-2-ethoxyphenyl]-3-[1-iodo-3-propynyl]-5-isopropylthiazolidin-4-one.

EXAMPLE A

Mycelial Inhibition

The compound was evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium monilofroma, Botrytis cinerea, Aspergillus niger* and *Ustilago hordeii.* Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a microsprayer with the fungicidal solution. The treated paper strips were incubated at 25° C. and the data is taken after 24 hours. Fungicidal activities were measured by a zone of inhibited mycelial growth from the center of the paper strip in terms of $mg/cm^2$ needed for 99% control of the fungus ($ED_{99}$). The effectiveness of the compound for fungicidal activity is reported in Table II in terms of the percent of the $ED_{99}$ of the test compound of the $ED_{99}$ of the standard Difolatan ®.

EXAMPLE B

Bean Powdery Mildew

The compound was tested for the control of the Bean Powdery Mildew organism *Erysiphe polygoni.* Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

EXAMPLE C

Tomato Late Blight

The compound was tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE D

Celery Late Blight

The Celery Late Blight test was conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

EXAMPLE E

Tomato Early Blight

The compound was tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a non-ionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table II.

EXAMPLE F

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a non-ionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table II.

EXAMPLE G

Bean Rust Eradicant

The compound was evaluated for their ability to eradicate Bean Rust caused by *Uromyces phaseoli tipica* on pinto beans.

Pinto beans plants variety Idaho 1–11, 16 (summer) or 19 (winter) days old were inoculated with a 50 ppm susension of uredospores in water containing a small amount of non-ionic surfactant. The inoculated plants were placed in an environmental chamber immediately after inoculation and incubated 20 hours. Following the incubation period, the plants were removed from the chamber and placed in a greenhouse maintained at 66°–68° F. and 60–80% relative humidity. Two days after inoculation, the plants were treated by spraying with a 200 ppm solution of test compound in an acetone and water carrier formulation containing a small amount of non-ionic surfactant. One or two replicate pots (each containing two plants) were used or each compound. In addition, one or two replicate pots were sprayed with the same carrier formulation (without a test compound) as a control (hereinafter "untreated checks"). The plants were kept in the greenhouse until evaluated. The plants were evaluated for disease control when disease symptoms were well developed on the untreated checks, normally about 14 days after treatment. The percentage disease control (or eradication) provided by a test compound was based on the percent disease reduction relative to the untreated checks. The results are reported in Table II.

TABLE I

Compounds of the formula:

$$IC\equiv CCH_2\text{-}N(C(=O)\text{-}C(R)\text{=}S\text{-}CR^2R^1)$$

| Compound | R | R¹ | R² | Physical State | %C Calc. | %C Found | %H Calc. | %H Found | %N Calc. | %N Found |
|---|---|---|---|---|---|---|---|---|---|---|
| 1 45634 | —H | —CH₂CH(CH₃)—(CH₂)₃CH(CH₃)₂ | —H | light brown oil | 45.80 | 45.54 | 6.11 | 6.39 | 3.56 | 3.56 |
| 2 45551 | —H | 2-(CH₃O)-C₆H₄— | —H | yellow solid, mp 95–100° C. | 41.82 | 44.98 | 3.22 | 4.42 | 3.75 | 4.05 |
| 3 45635 | —H | 4-(CH₃O)-C₆H₄— | —H | white solid, mp 98–100° C. | 41.82 | 39.58 | 3.22 | 4.36 | 3.75 | 3.9 |
| 4 43912 | —H | 2,4-(CH₃O)₂-C₆H₃— | —H | orange oil | 41.69 | 39.9 | 3.47 | 3.62 | 3.47 | 3.05 |
| 5 44301 | —H | 2-(CH₃CH₂O)-C₆H₄— | —H | red oil | 43.41 | 40.65 | 3.62 | 3.72 | 3.62 | — |
| 6 44404 | —H | 4-(CH₃CH₂O)-C₆H₄— | —H | orange oil | 43.41 | 40.23 | 3.62 | 3.99 | 3.62 | 3.12 |
| 7 45129 | —H | 4-Br-C₆H₄— | —H | orange oil | 34.12 | 33.91 | 2.13 | 2.35 | 3.32 | 3.17 |
| 8 45521 | —H | 3-Cl-C₆H₄— | —H | white fine crystals, mp 115–120° C. | 38.15 | 36.24 | 2.38 | 2.64 | 3.71 | 3.91 |
| 9 45517 | —H | 4-Cl-C₆H₄— | —H | yellow oil | 38.15 | 35.35 | 2.38 | 2.62 | 3.71 | 3.37 |
| 10 45339 | —H | 2,4-Cl₂-C₆H₃— | —H | beige crystalline solid, mp 109–114° C. | 34.95 | 37.51 | 1.94 | 2.35 | 3.40 | 3.49 |
| 11 45272 | —H | 3,4-Cl₂-C₆H₃— | —H | red glass | 34.95 | 36.12 | 1.94 | 2.31 | 3.39 | 1.97 |

TABLE I-continued

Compounds of the formula:

$$IC\equiv CCH_2-N(R^2)(CR^1)-C(=O)-C(R)-S-$$ (thiazolidinone-type ring)

| Compound | R | R¹ | R² | Physical State | % C Calc. | % C Found | % H Calc. | % H Found | % N Calc. | % N Found |
|---|---|---|---|---|---|---|---|---|---|---|
| 12  45338 | —H | 2,6-dichlorophenyl | —H | beige crystalline solid, mp 125–130° C. | 34.95 | 33.59 | 1.94 | 2.2 | 3.40 | 3.24 |
| 13  45271 | —H | 3-(trifluoromethyl)phenyl | —H | white solid, mp 90–93° C. | 37.96 | 37.67 | 2.19 | 2.31 | 3.41 | 2.86 |
| 14  45311 | —H | 4-cyanophenyl | —H | yellow solid, mp 151–156° C. | 42.39 | 44.95 | 2.44 | 2.92 | 7.61 | 7.89 |
| 15  45270 | —H | 4-(methylthio)phenyl | —H | brown oil | 40.10 | 38.32 | 3.08 | 2.94 | 3.60 | 2.79 |
| 16  45121 | —H | 4-(methylsulfonyl)phenyl | —H | beige solid | 37.05 | 37.39 | 2.85 | 3.49 | 3.33 | 2.65 |
| 17  45399 | —H | 3-nitrophenyl | —H | yellow crystalline solid, mp 98–105° C. | 37.11 | 36.77 | 2.32 | 2.92 | 7.22 | 7.62 |
| 18  45032 | —H | 4-biphenylyl | —H | white solid, mp 129–131° C. | 51.55 | 52.85 | 3.34 | 3.58 | 3.34 | 1.12 |
| 19  45175 | —H | 3-phenoxyphenyl | —H | light brown solid | 49.65 | 51.00 | 3.22 | 3.68 | 3.22 | 2.83 |
| 20  45124 | —H | 4-phenoxyphenyl | —H | light brown oil | 49.65 | 46.49 | 3.22 | 3.19 | 3.22 | 3.05 |

TABLE I-continued

Compounds of the formula:

$$IC{\equiv}CCH_2\underset{}{\overset{}{N}}{-}\underset{\underset{R^1}{|}}{\overset{\overset{O}{\|}}{C}}{-}\underset{S}{\overset{}{C}}{-}R$$
(with $R^2$ on the carbon bearing $R^1$)

| Compound | R | R¹ | R² | Physical State | % C Calc. | % C Found | % H Calc. | % H Found | % N Calc. | % N Found |
|---|---|---|---|---|---|---|---|---|---|---|
| 21 45314 | —H | 3-(2,4-dichlorophenoxy)phenyl | —H | light brown glass | 42.86 | 42.55 | 2.38 | 2.82 | 2.78 | 2.53 |
| 22 45341 | —H | 3-(3-trifluoromethylphenoxy)phenyl | —H | brown oil | 45.33 | 39.65 | 2.58 | 2.75 | 2.78 | 2.19 |
| 23 45254 | —H | 5-bromothien-2-yl | —H | beige solid, mp 78–84° C. | 28.04 | 29.09 | 1.64 | 1.72 | 3.27 | 2.75 |
| 24 43624 | —CH₃ | 2-methoxyphenyl | —H | brown oil | 43.41 | 47.34 | 3.62 | 4.58 | 3.62 | 3.48 |
| 25 44138 | —CH₃ | 2,4-dimethoxyphenyl | —H | yellow oil | 43.17 | 44.39 | 3.84 | 4.15 | 3.36 | 3.46 |
| 26 44298 | —CH₃ | 2-ethoxyphenyl | —H | orange oil | 44.89 | 41.18 | 3.99 | 3.87 | 3.49 | 3.06 |
| 27 43575 | —CH₃ | 4-ethoxyphenyl | —H | brown oil | 44.89 | 49.22 | 3.99 | 5.14 | 3.49 | 3.22 |
| 28 45120 | —CH₃ | 2,3,4-trimethoxyphenyl | —H | yellow solid | 42.95 | 42.38 | 4.03 | 4.32 | 3.13 | 2.85 |
| 29 45017 | —CH₃ | 2-chloro-4-methoxyphenyl | —H | yellow oil | 39.86 | 40.28 | 3.08 | 3.15 | 3.32 | 2.79 |

TABLE I-continued

Compounds of the formula:

$$IC{\equiv}CCH_2-\underset{\underset{R^1}{\overset{|}{R^2-C-S}}}{N}-\overset{\overset{O}{\parallel}}{C}-R$$

| Compound | R | R¹ | R² | Physical State | % C Calc. | % C Found | % H Calc. | % H Found | % N Calc. | % N Found |
|---|---|---|---|---|---|---|---|---|---|---|
| 30 44618 | —CH₃ | 4-SCH₃-C₆H₄— | —H | yellow oil | 41.69 | 42.65 | 3.47 | 4.09 | 3.47 | 3.17 |
| 31 43622 | —CH₃ | 3-CF₃-C₆H₄— | —H | brown oil | 39.53 | 41.54 | 2.59 | 3.04 | 3.29 | 3.0 |
| 32 43717 | —CH₃ | 3-Cl-C₆H₄— | —H | yellow oil | 39.85 | 36.99 | 2.81 | 2.92 | 3.58 | 3.2 |
| 33 43716 | —CH₃ | 4-Cl-C₆H₄— | —H | brown oil | 39.85 | 37.7 | 2.8 | 3.08 | 3.58 | 3.21 |
| 34 44739 | —CH₃ | 2,4-Cl₂-C₆H₃— | —H | brown oil | 36.62 | 33.36 | 2.35 | 2.53 | 3.29 | 2.64 |
| 35 43574 | —CH₃ | 3,4-Cl₂-C₆H₃— | —H | white solid mp 78–84° C. | 36.62 | 36.54 | 2.35 | 2.52 | 3.29 | 3.29 |
| 36 44541 | —CH₃ | 4-Br-C₆H₄— | —H | beige solid | 33.47 | 36.69 | 2.36 | 2.67 | 3.00 | 3.23 |
| 37 43576 | —CH₃ | 4-CN-C₆H₄— | —H | brown glass | 43.98 | 43.62 | 2.88 | 3.41 | 7.33 | 6.67 |
| 38 44571 | —CH₃ | 3-NO₂-C₆H₄— | —H | beige solid, mp 107–111° C. | 38.81 | 33.45 | 2.74 | 3.01 | 6.97 | 6.36 |
| 39 43715 | —CH₃ | 4-(PhCH₂O)-C₆H₄— | —H | yellow solid mp 115–120° C. | 51.84 | 50.81 | 3.89 | 4.34 | 3.02 | 2.9 |

TABLE I-continued

Compounds of the formula: $IC\equiv CCH_2-N(-C(=O)-C(-R)(-S-))-C(R^1)(R^2)$ (cyclic)

| Compound | R | R¹ | R² | Physical State | %C Calc. | %C Found | %H Calc. | %H Found | %N Calc. | %N Found |
|---|---|---|---|---|---|---|---|---|---|---|
| 40 43749 | —CH₃ | benzo-1,4-dioxane (2,3-dihydro-1,4-benzodioxin-6-yl) | —H | yellow solid mp 117–122° C. | 45.53 | 41.49 | 3.25 | 3.35 | 3.79 | 3.09 |
| 41 43623 | —CH₃ | 1-naphthyl | —H | gold solid | 50.12 | 51.37 | 3.44 | 4 | 3.44 | 2.95 |
| 42 44097 | —CH₃ | —(CH₂)₅CH₃ | —CH₃ | brown solid mp 55–60° C. | 44.33 | 43.97 | 5.8 | 6.07 | 3.69 | 3.86 |
| | | | | | 44.33 | 43.97 | 5.8 | 6.07 | 3.69 | 3.86 |
| 43 44070 | —CH₃ | 4-chlorophenyl | —CH₃ | oil | 41.43 | 39.21 | 3.21 | 3.39 | 3.45 | 3.17 |
| 44 43914 | —CH₃ | 2-thienyl | —H | orange oil | 36.36 | 34.83 | 2.75 | 3.58 | 3.86 | 3.31 |

TABLE II

FUNGICIDAL ACTIVITY

| Compound | Mycelial Inhibition Pyth. | Rhiz. | Fus. | Botr. | Asper. | Ustil | TLB | RB | TEB | CLB | BPM | BR |
|---|---|---|---|---|---|---|---|---|---|---|---|---|
| 1 45634 | 0 | 46 | 48 | 0 | 65 | 0 | 37 | 50 | 0 | 83 | 91 | 0 |
| 2 45551 | 0 | 31 | 0 | 0 | 64 | 0 | 98 | 0 | 20 | 95 | 0 | 0 |
| 3 45635 | 23 | 34 | 39 | 34 | 87 | 0 | 91 | 28 | 56 | 62 | 0 | 0 |
| 4 43912 | 0 | 0 | 0 | 0 | 0 | 0 | 96 | 0 | 57 | 95 | 0 | 0 |
| 5 44301 | 0 | 48 | 0 | 0 | 0 | 0 | 100 | 84 | 11 | 92 | 0 | 0 |
| 6 44404 | 17 | 38 | 0 | 0 | 54 | 0 | 92 | 0 | 0 | 88 | 0 | 0 |
| 7 45219 | 25 | 40 | 47 | 0 | 85 | 43 | 89 | 0 | — | 70 | 50 | 0 |
| 8 45521 | 30 | 39 | 0 | 20 | 0 | 0 | 94 | 25 | 38 | 96 | 100 | — |
| 9 45517 | 31 | 39 | 0 | 0 | 38 | 38 | 99 | 0 | 42 | 100 | 100 | — |
| 10 45339 | 0 | 0 | 0 | 0 | 42 | 0 | 98 | 50 | 55 | 96 | 50 | 0 |
| 11 45272 | 15 | 43 | 0 | 30 | 43 | 20 | 69 | 0 | 65 | 0 | 69 | 0 |
| 12 45338 | 0 | 16 | 0 | 19 | 0 | 0 | 100 | 50 | 0 | 85 | 58 | 0 |
| 13 45271 | 16 | 100 | 0 | 0 | 0 | 0 | 88 | 88 | 0 | 100 | 100 | 0 |
| 14 45311 | 29 | 38 | 0 | 0 | 28 | 0 | 91 | 20 | — | 93 | 0 | 0 |
| 15 45270 | 0 | 43 | 0 | 19 | 0 | 0 | 96 | 75 | 25 | 93 | 0 | 0 |
| 16 45121 | 0 | 0 | 0 | 0 | 0 | 0 | 79 | 30 | 0 | 20 | 0 | 0 |
| 17 45399 | 14 | 33 | 0 | 0 | 0 | 0 | 98 | 42 | 33 | 70 | 0 | — |
| 18 45032 | 19 | 100 | 50 | 33 | 57 | 0 | 96 | 0 | 17 | 94 | 0 | 0 |
| 19 45175 | 0 | 29 | 0 | 0 | 0 | 0 | 100 | 81 | 88 | 82 | 0 | 0 |
| 20 45124 | 0 | 30 | 68 | 19 | 0 | 0 | 97 | 50 | 33 | 60 | 0 | 0 |
| 21 45314 | 0 | 40 | 0 | 0 | 0 | 0 | 31 | 0 | — | 83 | 0 | 0 |
| 22 45341 | 0 | 0 | 0 | 0 | 0 | 0 | 98 | 25 | 0 | 85 | 88 | 0 |
| 23 45254 | 20 | 62 | 26 | 25 | 91 | 20 | 91 | 0 | 42 | 90 | 7 | 0 |
| 24 43624 | 13 | 0 | 0 | 0 | 0 | 0 | 93 | 0 | 44 | 60 | 44 | 0 |
| 25 44138 | 0 | 60 | 0 | 30 | 17 | 0 | 98 | 77 | 83 | 39 | 0 | 0 |
| 26 44298 | 0 | 48 | 0 | 0 | 0 | 0 | 98 | 89 | 0 | 79 | 0 | 0 |
| 27 43575 | 0 | 38 | 0 | 0 | 0 | 0 | 100 | 64 | 92 | 58 | 17 | 0 |
| 28 45120 | 0 | 0 | 0 | 0 | 0 | 0 | 94 | 0 | 0 | 30 | 0 | 0 |
| 29 45017 | 0 | 49 | 0 | 24 | 0 | 0 | 95 | 63 | 11 | 99 | 69 | 0 |
| 30 44618 | 0 | 0 | 0 | 0 | 0 | 0 | 100 | 0 | 75 | 30 | 0 | 0 |
| 31 43622 | 36 | 0 | 0 | 0 | 0 | 0 | 50 | 0 | 85 | 70 | 60 | 0 |
| 32 43717 | 34 | 83 | 0 | 68 | 65 | 18 | 98 | 55 | 19 | 84 | 100 | 0 |
| 33 43716 | 29 | 39 | 0 | 31 | 0 | 13 | 98 | 88 | 44 | 50 | 53 | 0 |
| 34 44739 | 15 | 44 | 0 | 23 | 0 | 0 | 98 | 40 | 0 | 94 | 91 | 0 |

TABLE II-continued
FUNGICIDAL ACTIVITY

| Compound | Mycelial Inhibition | | | | | | TLB | RB | TEB | CLB | BPM | BR |
| --- | --- | --- | --- | --- | --- | --- | --- | --- | --- | --- | --- | --- |
| | Pyth. | Rhiz. | Fus. | Botr. | Asper. | Ustil | | | | | | |
| 35 43574 | 0 | 73 | 0 | 0 | 0 | 0 | 100 | 60 | 0 | 53 | 58 | 0 |
| 36 44541 | 0 | 50 | 0 | 0 | 0 | 0 | 99 | 30 | 63 | 95 | 0 | 0 |
| 37 43576 | 0 | 53 | 0 | 0 | 0 | 0 | 100 | 44 | 33 | 58 | 0 | 0 |
| 38 44571 | 13 | 0 | 0 | 0 | 0 | 0 | 99 | 0 | 88 | 93 | 0 | 0 |
| 39 43715 | 0 | 20 | 0 | 0 | 0 | 0 | 96 | 63 | 0 | 40 | 0 | 0 |
| 40 43749 | 27 | 0 | 0 | 0 | 0 | 0 | 100 | 0 | 19 | 57 | 0 | 0 |
| 41 43623 | 29 | 0 | 0 | 0 | 0 | 0 | 96 | 0 | 44 | 85 | 20 | 0 |
| 42 44097 | 0 | 88 | 69 | 37 | 107 | 0 | 88 | — | 0 | 90 | 0 | 0 |
| 43 44070 | 0 | 52 | 0 | 0 | 0 | 0 | 97 | 0 | 90 | 63 | 0 | 0 |
| 44 43914 | 0 | 0 | 0 | 0 | 0 | 0 | 89 | 0 | 0 | 86 | 0 | 0 |

Pyth. = *Pythium ultimum*
Rhiz. = *Rhizoctonia solani*
Fusar. = *Fusarium moniloforme*
Botr. = *Botrytis cinerea*
Asper. = *Aspergillus niger*
Ustil. = *Ustilago hordeii*
— = *Not tested or test failed*
TLB - Tomato Late Blight (*Phytophthora infestans*)
RB - Rice Blast (*Piricularia oryzae*)
TEB - Tomato Early Blight (*Alternaria solani conidia*)
CLB - Celery Late Blight (*Septoria apii*)
BPM - Bean Powdery Mildew (*Erysiphe polygoni*)
BR - Bean Rust (*Uromyces phaseoli tipica*)

What is claimed is:

1. A compound of the formula:

$$IC\equiv CCH_2N-\overset{R^2}{\underset{R^1}{\big|}}S-\overset{R^3}{\underset{R}{\big|}}-{=}O$$

wherein R is hydrogen, lower alkyl; or aryl or aralkyl having from 6 to 12 carbon atoms, optionally substituted with one to three substituents, each independently with one to three substituents, each independently selected from halogen, cyano, lower alkyl, lower alkoxy, nitro or trihalomethyl; $R^1$ is alkyl having from 1 to 12 carbon atoms, cycloalkyl having from 3 to 8 carbon atoms; aryl or aralkyl having from 6 to 12 carbon atoms optionally substituted with one to three substituents, each independently selected from halogen, cyano, lower alkyl, lower alkoxy, nitro, trihalo-substituted methyl, phenyl, phenoxy, substituted phenoxy substituted with 1 to 3 substituents independently selected from halogen, lower alkyl, lower alkoxy or trihalomethyl, benzyloxy, lower alkylthio, lower alkylsulfinyl, lower alkylsulfonyl, arylthio ($C_6$ to $C_{12}$), or two lower alkoxy groups joined to give an alkylene bridge; or thiophene or furanyl either opionally substituted with 1 to 3 substituents independently selected from halogen, trihalomethyl, lower alkyl, lower alkoxy; $R^2$ is hydrogen, lower alkyl, cycloalkyl having from 3 to 8 carbon atoms, or aryl or aralkyl having from 6 to 12 carbon atoms optionally substituted with one to three substituents, each independently selected from halogen, cyano, lower alkyl, lower alkoxy, nitro or trihalomethyl; and $R^3$ is hydrogen or lower alkyl.

2. A compound according to claim 1 wherein R is hydrogen, lower alkyl or phenyl.

3. A compound according to claim 2 wherein $R^3$ is hydrogen or methyl.

4. A compound according to claim 3 wherein $R^1$ is substituted aryl.

5. A compound according to claim 4 wherein $R^2$ is hydrogen or lower alkyl.

6. A compound according to claim 5 wherein R is hydrogen or methyl, and $R^2$ is hydrogen or methyl.

7. A compound according to claim 6 wherein $R^3$ is hydrogen.

8. A compound according to claim 7 wherein R and $R^2$ are hydrogen.

9. A compound according to claim 8 wherein $R^1$ is 2-ethoxyphenyl.

10. A compound according to claim 7 wherein R is methyl and $R^2$ is hydrogen.

11. A compound according to claim 10 wherein $R^1$ is 3,4-dichlorophenyl.

12. A compound according to claim 10 wherein $R^1$ is 2,4-dichlorophenyl.

13. A compound according to claim 10 wherein $R^1$ is 1-naphthyl.

14. A method of controlling fungi which comprises contacting said fungi or their growth environment with a fungicidally effective amount of a compound of claim 1.

15. A method of controlling fungi which comprises contacting said fungi or their growth environment with a fungicidally effective amount of a compound of claim 4.

16. A method of controlling fungi which comprises contacting said fungi or their growth environment with a fungicidally effective amount of a compound of claim 7.

17. A method of controlling fungi which comprises contacting said fungi or their growth environment with a fungicidally effective amount of a compound of claim 9.

18. A method of controlling fungi which comprises contacting said fungi or their growth environment with a fungicidally effective amount of a compound of claim 11.

19. A method of controlling fungi which comprises contacting said fungi or their growth environment with a fungicidally effective amount of a compound of claim 12.

20. A fungicidal composition which comprises a biologically inert carrier and a fungicidally effective amount of a compound of claim 1.

21. A fungicidal composition which comprises a biologically inert carrier and a fungicidally effective amount of a compound of claim 4.

22. A fungicidal composition which comprises a biologically inert carrier and a fungicidally effective amount of a compound of claim 7.

23. A fungicidal composition which comprises a biologically inert carrier and a fungicidally effective amount of a compound of claim 9.

24. A fungicidal composition which comprises a biologically inert carrier and a fungicidally effective amount of a compound of claim 11.

25. A fungicidal composition which comprises a biologically inert carrier and a fungicidally effective amount of a compound of claim 12.

* * * * *